(12) United States Patent
Flaherty et al.

(10) Patent No.: US 11,559,593 B2
(45) Date of Patent: Jan. 24, 2023

(54) ULTRAVIOLET DISINFECTION DEVICE

(71) Applicant: Germbot, LLC, Bettendorf, IA (US)

(72) Inventors: Patrick Flaherty, Bettendorf, IA (US);
Karen Flaherty, Bettendorf, IA (US);
Conor Flaherty, Bettendorf, IA (US);
Bruce Winkler, Madison, WI (US);
Tim Bank, Fitchburg, WI (US)

(73) Assignee: Germbot, LLC, Bettendorf, IA (US)

( * ) Notice: Subject to any disclaimer, the term of this patent is extended or adjusted under 35 U.S.C. 154(b) by 187 days.

(21) Appl. No.: 16/162,189

(22) Filed: Oct. 16, 2018

(65) Prior Publication Data
US 2019/0111169 A1    Apr. 18, 2019

Related U.S. Application Data

(60) Provisional application No. 62/573,489, filed on Oct. 17, 2017.

(51) Int. Cl.
*A61L 2/10* (2006.01)
*A61L 9/20* (2006.01)
*G06F 3/0346* (2013.01)
*H01J 61/72* (2006.01)

(52) U.S. Cl.
CPC .............. *A61L 2/10* (2013.01); *G06F 3/0346* (2013.01); *A61L 9/20* (2013.01); *A61L 2202/11* (2013.01); *A61L 2202/14* (2013.01); *A61L 2202/16* (2013.01); *H01J 61/72* (2013.01)

(58) Field of Classification Search
CPC .... A61L 2/10; A61L 2202/16; A61L 2202/11; A61L 9/20; A61L 2202/14; G06F 3/0346; G06F 3/016; H01J 61/72
See application file for complete search history.

(56) References Cited

U.S. PATENT DOCUMENTS

| | | | |
|---|---|---|---|
| 3,975,790 A | 8/1976 | Patterson | |
| 6,239,442 B1 | 5/2001 | Iimura | |
| 7,444,711 B2 | 11/2008 | Garcia et al. | |
| 7,476,885 B2 | 1/2009 | Garcia et al. | |
| 7,581,283 B2 | 9/2009 | Yoo et al. | |
| 8,029,739 B2 * | 10/2011 | Field | A47L 11/283 422/22 |
| 8,112,841 B2 * | 2/2012 | Garcia | A47L 9/02 15/319 |

(Continued)

OTHER PUBLICATIONS

Extech Tachometer (Year: 2008).*

(Continued)

*Primary Examiner* — Sean E Conley
*Assistant Examiner* — Brendan A Hensel
(74) *Attorney, Agent, or Firm* — Charles S. Sara; Elizabeth L. Neal; DeWitt LLP

(57) ABSTRACT

The present device provides a safe, effective means of mobile ultraviolet (UV) disinfection. A control board within the main body of the device receives data from sensors that may variously measure orientation and speed of the main body as it moves along various surfaces for disinfection. In response to such data, the control board may brighten, dim, or completely shut off UV light-emitting diodes (UVLEs), both to prevent over- and under-exposure of the materials being disinfected, and to prevent a user from unsafely using the device.

19 Claims, 6 Drawing Sheets

(56) References Cited

U.S. PATENT DOCUMENTS

| | | | |
|---|---|---|---|
| 8,226,887 B2 * | 7/2012 | Harmon | A61L 2/10 250/455.11 |
| 8,302,248 B2 * | 11/2012 | Chavana, Jr. | A47L 9/00 134/1 |
| 8,330,121 B2 * | 12/2012 | Douglas | A61L 2/10 250/455.11 |
| 8,481,985 B2 | 7/2013 | Neister | |
| 8,975,605 B2 | 3/2015 | Neister | |
| 2006/0216193 A1 | 9/2006 | Johnson et al. | |
| 2008/0052872 A1 * | 3/2008 | Cho | A47L 9/122 15/421 |
| 2008/0061252 A1 * | 3/2008 | Garcia | A61L 2/10 250/504 H |
| 2008/0065468 A1 * | 3/2008 | Berg | G06Q 30/02 705/7.32 |
| 2008/0073595 A1 | 3/2008 | Thiruppathi | |
| 2013/0198991 A1 | 8/2013 | Cadigan | |
| 2016/0175475 A1 * | 6/2016 | DuPuis | F21V 14/08 250/432 R |
| 2018/0064594 A1 * | 3/2018 | Finch, Jr. | A61G 7/057 |

OTHER PUBLICATIONS

Extech Tachometer supplement (Year: 2013).*
Hackaday (Year: 2017).*
Standex Electronics (Year: 2015).*

* cited by examiner

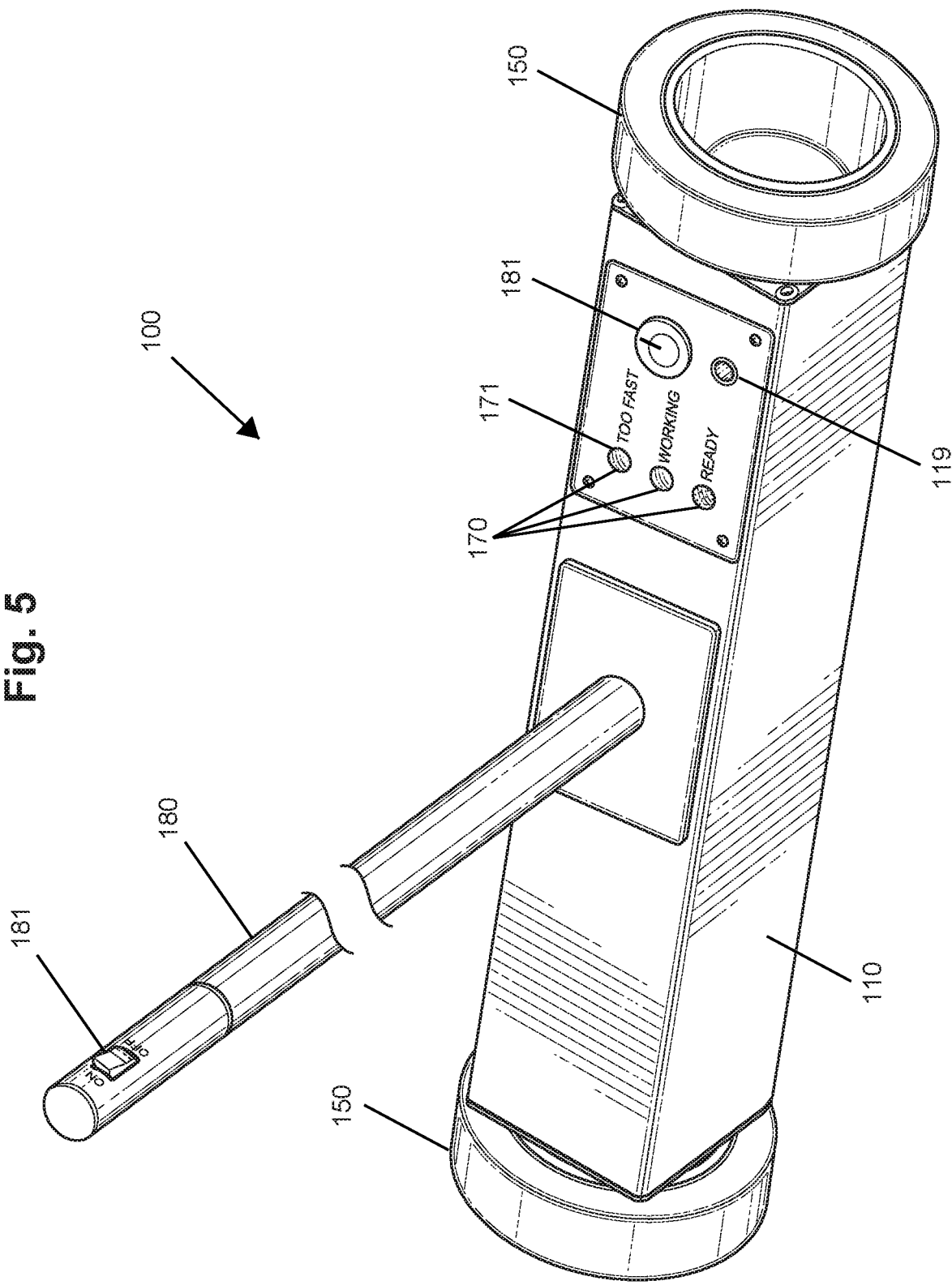

ULTRAVIOLET DISINFECTION DEVICE

CROSS-REFERENCE TO RELATED APPLICATIONS

This application claims the benefit of prior-filed, U.S. Provisional Patent Applications No. 62/573,489, filed on Oct. 17, 2017, the contents of which are incorporated herein by reference in their entirety.

BACKGROUND OF THE INVENTION

The present invention is generally directed to an apparatus for sterilizing objects. Specifically, the present invention is directed to a rolling device with an ultraviolet disinfection unit.

The need for cleaning athletic and other types of mats and floor surfaces has spawned many cleaning products and systems, some automated and some manual. In some of these systems, ultraviolet (UV) light is used to irradiate a surface in order to kill pathogens such as bacteria and viruses. UV light has the advantages of being quick and easy to apply, leaving no chemical residue, being in unlimited supply for as long as there is power to the system, and being better for surfaces that may be stained or otherwise damaged by liquid disinfectants.

Unfortunately, most of these inventions have not accounted for the needs of the marketplace or safety considerations. These devices utilize mercury vapor lamps, which can release hazardous mercury fumes if broken, a significant danger in a device intended to pass closely over large swathes of a floor for extended periods of time. These devices do not account for differences in speed as they pass over the surface, which can lead to some surfaces being underexposed, resulting in inadequate disinfection. Overexposure may cause UV damage to the surface. Furthermore, these devices often lack safety features, allowing a user to accidentally expose themselves or others to UV light, which can cause injury.

It is therefore an object of the present invention to provide a UV disinfection system that utilizes safer UV light emitters (UVLEs), and has safety features to prevent damage to surfaces or injury to users while still ensuring adequate disinfection.

BRIEF SUMMARY

The ultraviolet disinfection device includes a main body having a hollow configuration divided into a control compartment and an active compartment. A handle is connected to the main body. At least one control board is located within the control compartment, while a heat sink is located within the main body. At least one UVLE panel is operably connected to the heat sink and operably connected to the control board. Each UVLE panel comprises at least one UVLE. A plurality of end plates are removably attached to a first side and a second side of the main body, with a plurality of wheel assemblies connected to the main body. At least one speed sensor is operably connected to the control board. The speed sensor is configured to detect data on the speed of the main body and transmit this data to the control board.

BRIEF DESCRIPTION OF THE DRAWINGS

FIGS. 1, 2, 3a, 3b, 4, and 5 are bottom perspective, exploded, side cross-sectional, side cross-sectional, top cross-sectional, and top perspective views, respectively, of an embodiment of a UV disinfection device.

DETAILED DESCRIPTION OF THE INVENTION

Figure 1:
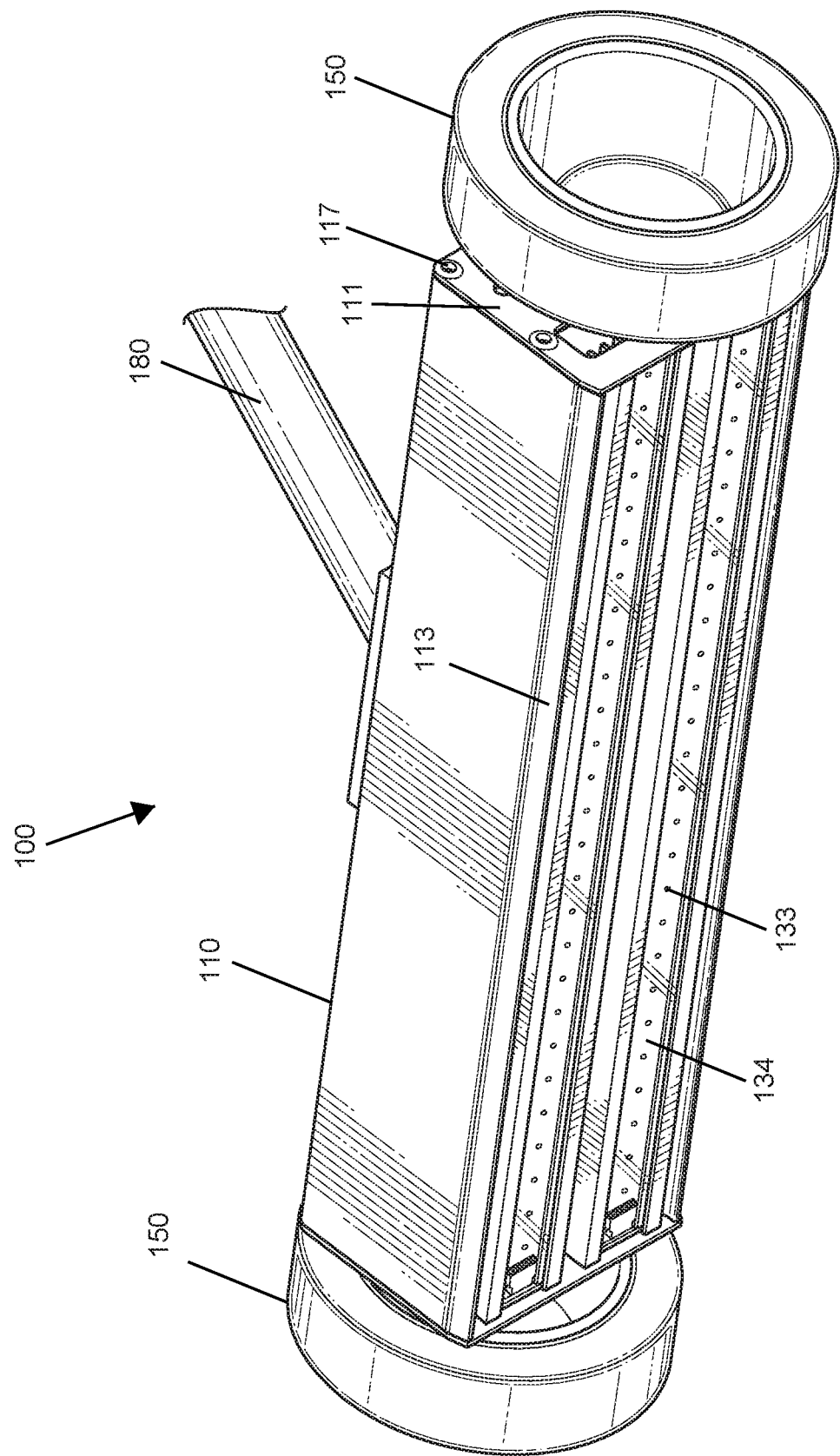
Figure 2:
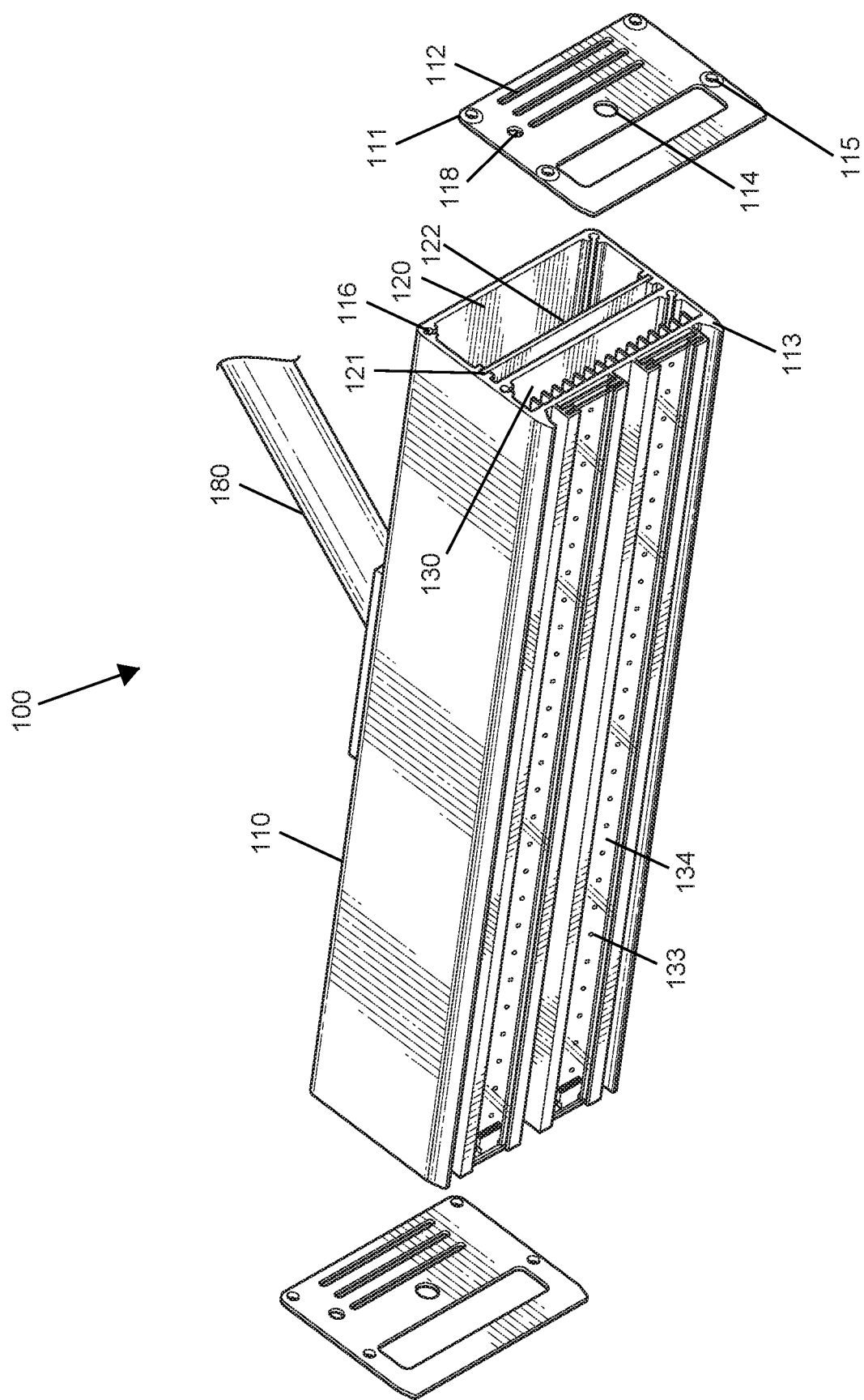

The present invention is a UV disinfection device 100. As can be seen in FIGS. 1 through 5, device 100 includes a main body 110 with a control compartment 120 and an active compartment 130. In certain embodiments, control compartment 120 and active compartment 130 are separated by a separation panel 140. Wheel assemblies 150 are mounted to either side of main body 110, along with at least one speed sensor 160 and at least one optional feedback system 170. Device 100 is manually driven by a user using handle 180 or driven by a motor assembly 190 attached to wheel assemblies 150.

In the exemplary embodiment, main body 110 is a hollow, elongated body having open ends for at least one of the left and right sides. In various embodiments, main body 110 may be manufactured from polymer, steel, or aluminum. Main body 110 may be a one-piece extrusion, multiple interconnected pieces, or any combination thereof. End plates 111, at least one of which is removable, at least partially close off the open side end or ends of main body 110. End vents 112 in end plates 111 allow a measure of ventilation of the interior of main body 110. The exterior edges of the lower level of main body 110 below active compartment 130 have two protruding rims 113 which have a slight incurvate deflection. The rims 113 are of equal length and inward orientation and form an open channel along the bottom side of main body 110. In certain embodiments, a UV-inert, flexible, and/or collapsible skirt made from a material such as, but not limited to, fabric or a sheet or sheets of polymer, may be attached on or around the bottom of main body 110 provide the user with additional protection from UV light.

Each end plate 111 includes a wheel aperture 114 and a plurality of attachment apertures 115. Each attachment apertures 115 aligns with an attachment channel 116 to allow removable attachment members 117 to extend through, attaching end plate 111 to main body 110. In the exemplary embodiment, attachment channels 116 are c-shaped channels, while attachment members 117 are screws. Other embodiments of attachment channels 116 may be threaded nuts or annuluses, unthreaded annuluses or channels, snap receivers, or any other mechanical connector receiver known in the art. Other embodiments of attachment members 117 may be bolts, snap fasteners, or any other mechanical connector known in the art. An optional sensor aperture 118 allows mounting of speed sensor 160 and/or wired communication between speed sensor 160 and the interior of control compartment 120. An optional charging port 119 allows recharge of the device 100 between uses.

Control compartment 120 and active compartment 130 extend lengthwise and parallel to each other over the entire length and width of main body 110. Control compartment 120 extends over active compartment 130. In certain embodiments, separation panel 140 is a solid planar panel that is permanently or removably connected at an approximately right angle to both front and rear interior surfaces of main body 110.

Control compartment 120 includes two board channels 121 extending lengthwise, parallel and opposite to each other on the front and rear interior surfaces of control compartment 120. Board channels 121 are offset from separation panel 140. Board channels 121 provide a secure slide-in location for at least one control board 122, such as, but not limited to, a printed circuit board (PCB) or multiple PCBs, to be inserted within board channels 121 and held in place within control compartment 120. A rechargeable or replaceable power source 123 such as, but not limited to, a battery or battery pack, is also located within control compartment 120.

The area above control board 122 provides airflow for ventilation and cooling of control board 122 and power source 123 as well as providing a physical offset from any heat that might dissipate from separation panel 140. Since power source 123 is located within control compartment 120, this reduces the likelihood that power source 123 will incur damage from overheating. In certain embodiments, control board 122 may include or otherwise be connected to an orientation sensor 124 for safety. Control board 122 is configured to adjust the power provided to any UVLEs 133 based on orientation data received from the at least one orientation sensor. In other words, if device 100 deviates from a base orientation beyond an acceptable amount, control board 122 will not allow device 100 to produce UV light. The deviation threshold may range from approximately 1 degree to approximately 45 degrees depending upon the construction of device 100. In certain embodiments, the base orientation is horizontal; other embodiments may allow the user to change the base orientation and/or deviation threshold to accommodate other, non-horizontal surfaces. Orientation sensor 124 may include sensors such as, but not limited to, a tilt switch or a single- or multi-axial accelerometer.

Active compartment 130 may have separation panel 140 as an upper boundary and a heat sink in the form of a heat sink panel 131 as a lower boundary. In the exemplary embodiment, heat sink panel 131 is integral to main body 110. In other embodiments, heat sink panel 131 may be removably held in place by channels similar to board channels 121. In certain embodiments, the heat sink may be located in portions of main body 110 other than the lower boundary of active compartment 130. The upper surface of heat sink panel 131 includes a series of multiple ridges running adjacent but separated from each other and parallel to each other to form a series of heat sink structures 132. The lower surface of heat sink panel 131 has a flat surface, and, in the exemplary embodiment, includes pre-punched connection holes to allow connection between control board 122 and at least one UVLE panel 134.

In the exemplary embodiment, each UVLE panel 134 is a circuit board operably connected to control board 122 and including at least one UVLE 133. In the exemplary embodiment, UVLEs 133 are solid-state light emitters such as, but not limited to, light-emitting diodes (LEDs). In certain embodiments, at least one UVLE 133 emits UVC light. UVC light is UV light with a wavelength ranging from approximately 100 nm to approximately 280 nm. In one such embodiment, at least one UVLE 133 emits UV light with a wavelength of approximately 250 nm. In certain embodiments, at least one UVLE panel 134 may be backed by a metallic backing plate 138, such as, but not limited to, a steel or an aluminum plate, to strengthen UVLE panel 134 and assist in conducting heat away from UVLE panel 134. The heat sink structures 132 take up and dissipate any heat generated by any UVLEs 133 on UVLE panels 134.

Figure 3A:
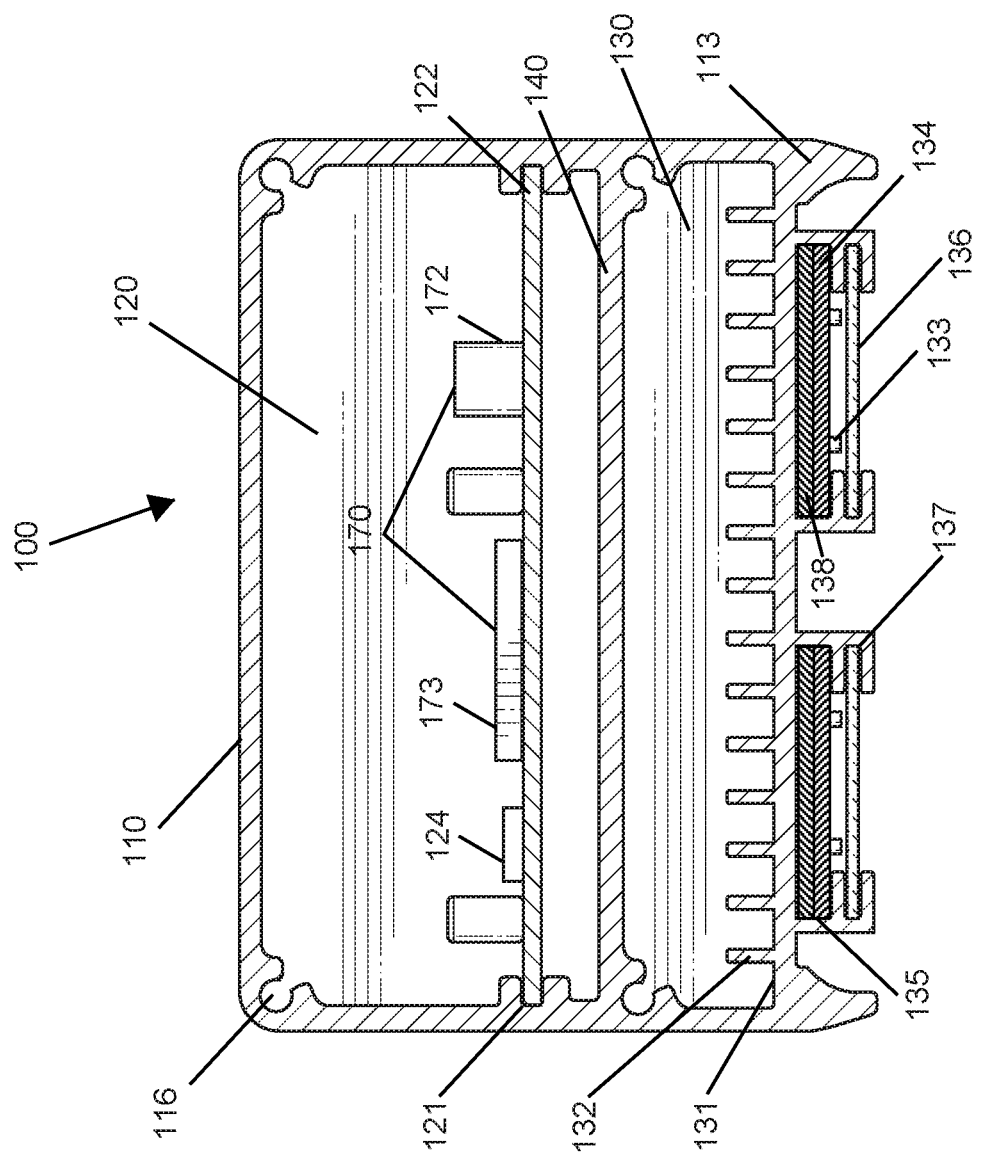

In the embodiment shown in FIG. 3*a*, each UVLE panel 134 is held adjacent and parallel to the lengthwise orientation of heat sink panel 131 by two of a plurality of UVLE channels 135. This embodiment includes two pairs of UVLE channels 135 to hold two UVLE panels 134, though other embodiments can include more or fewer UVLE panels 134 and respective UVLE channels 135. Each pair of UVLE channels 135 extends lengthwise, parallel and opposite to each other in active compartment 130. UVLE channels 135 are offset from heat sink panel 121. UVLE channels 135 provide a secure slide-in location for each UVLE panel 134, similar to control board 122 within board channels 121.

Each UVLE panel 134 is covered by an UVLE shield 136, a panel substantially transparent to UV light which protects UVLEs 133 from damage. In the exemplary embodiment, UVLE shields 136 are slabs of quartz glass; other embodiments may use different UV-transparent materials. Each UVLE shield 136 is held adjacent and parallel to the lengthwise orientation of a UVLE panel 134 by two shield channels 137. The exemplary embodiment includes two pairs of shield channels 137 to hold two UVLE shields 136, though other embodiments can include more or fewer shield channels 137 and UVLE shields 136. Each pair of shield channels 137 extends lengthwise, parallel and opposite to each other in active compartment 130. Shield channels 137 are located directly below UVLE channels 135. Shield channels 137 provide a secure slide-in location for each UVLE shield 136, similar to control board 122 within board channels 121.

Figure 3B:
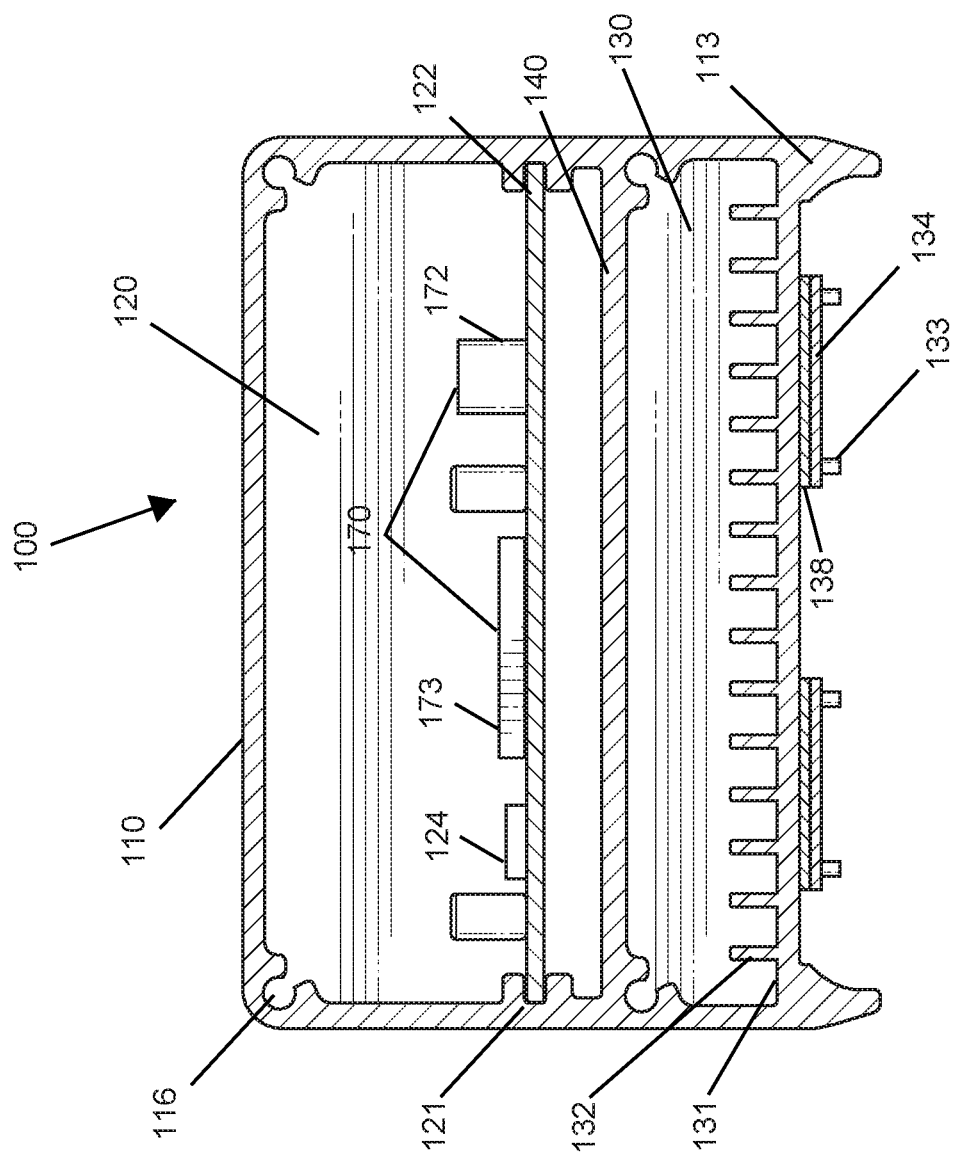
Figure 4:
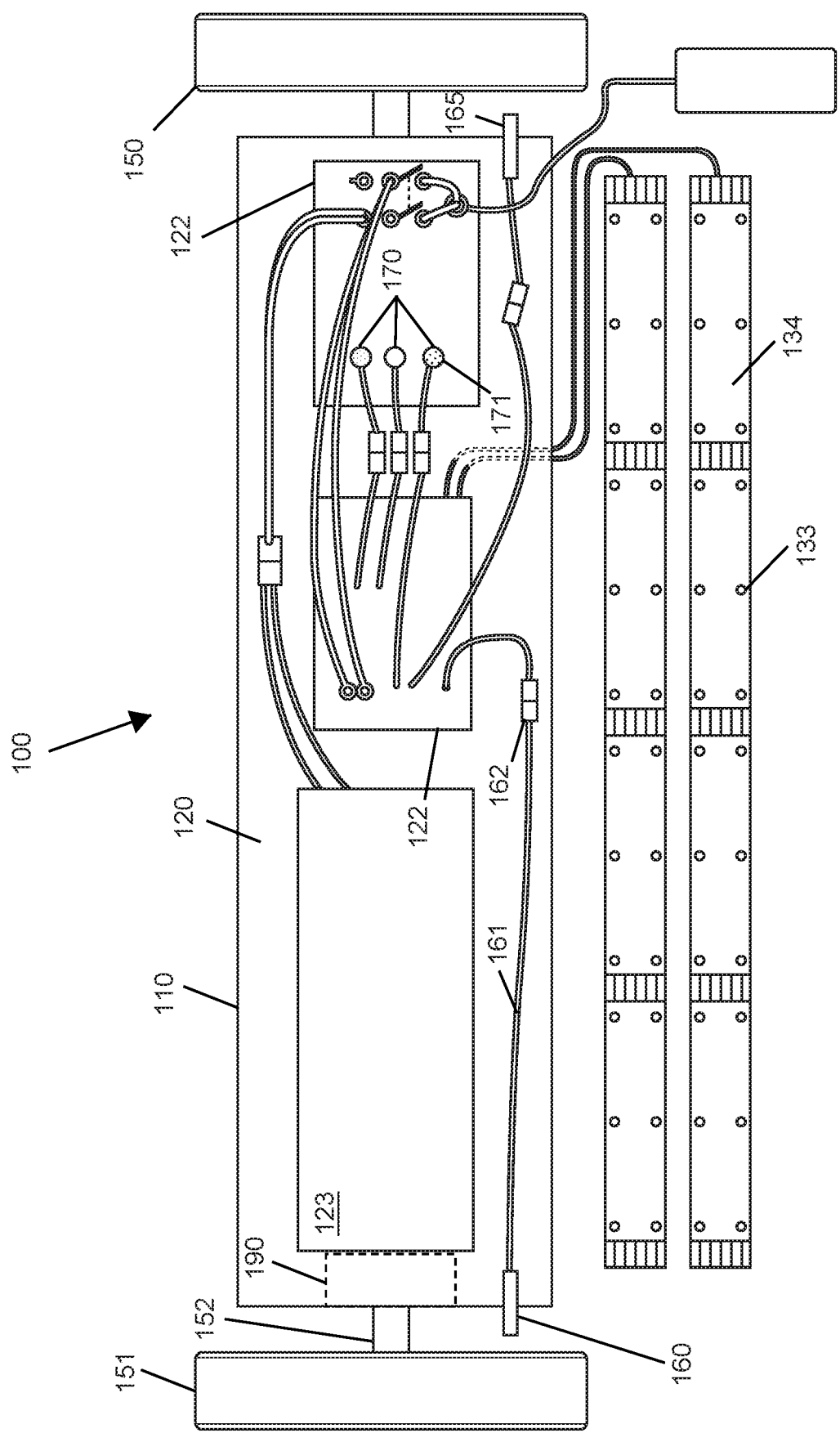

In the embodiment shown in FIG. 3*b*, the backing plate 138 of each UVLE panel 134 is directly connected to heat sink panel 131. While the embodiment shown in FIG. 3*b* does not show a UVLE shield 136, one may be incorporated over UVLE panel 134. Any of the various aspects of the embodiment shown in FIG. 3*a* may be combined with the embodiment shown in FIG. 3*b*, and vice versa.

In the exemplary embodiment, each wheel assembly 150 includes a wheel 151 mounted to a wheel axle 152. In this embodiment, wheel assembly 150 includes at least one motor driven wheel 151 that moves device 100 by electrical power using motor assembly 190. In another embodiment, wheel assembly 150 includes ball rollers that provide multilateral motion for device 100. In another embodiment, wheel axle 152 is slidably connected to a wheel axle connector which extends through wheel axle 152 and wheel aperture 114. In such an embodiment, the wheel axle connector is a press-release connector, when pressed allowing wheel axle 152 to slide up and down to adjust the height of main body 110 above a treatment surface.

At least one speed sensor 160 is located on or within main body 110. In one embodiment, speed sensor 160 is located on control board 122. In one embodiment, speed sensor 160 is located on end plate 111 adjacent to wheel 151. Various embodiments of speed sensor 160 may include a single- or multi-axial accelerometer, a light sensor that detects motion of wheel 151 via alternating colors on the surface of wheel 151, a laser motion sensor that detects surface motion of wheel 151, a physical roller contact sensor that reads the rotations and speed of a wheel or roller, or a magnetic sensor such as, but not limited to a reed switch with a rotation magnet on wheel 151.

Control board 122 processes input from speed sensor 160 to control UVLEs 133 and provides optional feedback through optional feedback system 170. In embodiments where speed sensor 160 is not connected directly to control board 122, a connector cable 161, such as, but not limited to, a cable or wire, connects speed sensor 160 to sensor connector 162, which is in turn connected to control board 122. In other embodiments, connector cable 161 connects speed sensor 160 directly to a sensor pad on control board 122. Certain embodiments may also include at least one height sensor 165 mounted to main body 110 to incorporate height into UV treatment optimization calculations.

Certain embodiments may include a feedback system 170 connected to main body 110 or handle 180 for providing to the user feedback regarding the speed and/or status of device 100. Feedback system 170 may include any combination of at least one haptic feedback output 171, at least one visual feedback output 172, and/or at least one audio feedback output 173. Haptic feedback outputs 171 may include vibration or braking modules for changing vibration transmitted through main body 110 and/or handle 180 or altering resistance to movement of wheels 151 using motor assembly 190. Visual feedback outputs 172 may include light emitters that indicate speed with changing color, intensity, or number or type of light emitters lit, or a light emitting or analog gauge or dial showing a readout of speed. Visual feedback outputs 172 may also include light emitters that indicate whether the UVLEs 133 and overall device 100 have power, or if recharging device 100 is necessary. Audio feedback outputs 173 may include speakers for emitting sounds ranging from a tone that changes volume or frequency, to a verbal warning of speed outside of parameters, to a verbal declaration of current speed at various intervals. Audio feedback outputs 173 may also include speakers for emitting sounds that indicate whether the UVLEs 133 and overall device 100 have power, or if recharging device 100 is necessary.

Handle 180 is attached to the rear panel of main body 110 to propel and/or steer device 100. In certain embodiments, handle 180 can rotate for better maneuvering, as with, by way of non-limiting example, a pin joint or a ball-and-socket joint. In other embodiments, the length of handle 180 is adjustable for better user ergonomics. Adjustment may occur through telescoping segments or adding or removing one or more detachable segments to or from handle 180. In certain embodiments, handle 180 includes a power switch 181 operably connected to control board 122 and/or UVLEs 133 to activate these components. In other embodiments, power switch 181 is located on main body 110. In certain embodiments, handle 180 is removable.

Device 100 is designed to provide specific capabilities and UV irradiation accuracy. First, device 100 uses UVLEs 133 instead of the standard delicate, potentially hazardous mercury vapor lamps used in the UV sterilization industry. Furthermore, device 100 controls delivery of UV light based on data from speed sensor 160. As a result, device 100 can manage on-off operations, safety interlock functions (to limit exposure of the device user) and speed control feedback to the user with the use of haptic, audio, and/or visual outputs. Device 100 provides adjustable UV irradiation level capability based upon the speed of the rolling motion of device 100 over a surface. In embodiments using motor assembly 190, device 100 may also control the speed at which its wheels 151 rotate to ensure effective disinfection.

Moreover, device 100 can provide a moment to moment (real time) constant irradiation level regardless of its speed over a surface by controlling (again in real time) adjustable UVLE 133 radiation intensity based on speed. Device 100 utilizes an algorithm to control transmission of UV radiation based on at least one of device speed, distance of UVLEs 133 to the cleaning surface, and power to the UVLEs. Device 100 uses at least one speed sensor 160 which can determine when the UVLEs 133 turn on or off. By way of non-limiting example, if the rolling speed of device 100 approaches, or exceeds, a speed which does not allow a proper UV irradiation level from device 100, feedback system 170 is activated, providing an indication to the user to slow movement of device 100. The same speed sensor(s) 160 further provides the basis for a safety interlock based on speed or no speed of device 100 (i.e. control board 122 turns off UVLEs 133 unless a minimum speed is detected by one or both wheels 151).

Furthermore, device 100 may have an adjustment to increase or decrease the height level of UVLEs 133 above the surface. This feature ensures the optimal motion of device 100 over various types of surfaces and keeps UVLEs 133 as close to the surface as possible when set correctly. The integral controller system for device 100 on control board 122 may utilize an algorithm which senses the height adjustment and the moment to moment speed of device 100 to provide the optimal power setting to the UVLEs 133. This combination of features provides an automatic uniform cleaning of surfaces beneath device 100. Device 100 provides accurate cleaning protocols which are not found with other UV products.

As seen in the accompanying drawings, the direct and simple functionality of device 100 provides a novel, unique and unobvious solution to providing an optimized UV disinfection device that can be pushed like a broom but has all the safeguards and cleaning abilities needed without having the user maintain more than minimal vigilance in the operation of device 100.

Any version of any component or method step of the invention may be used with any other component or method step of the invention. The elements described herein can be used in any combination whether explicitly described or not. All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within the range, whether specifically disclosed or not. Further, these numerical ranges should be construed as providing support for a claim directed to any number of subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

The devices, methods, compounds and composition of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting.

What is claimed is:

1. An ultraviolet disinfection device comprising:
    a main body having a hollow configuration divided into a control compartment and an active compartment;
    a handle connected to the main body;

at least one control board located within the control compartment;

a heat sink located within the active compartment of the main body, wherein the heat sink comprises a plurality of heat sink structures located on a first side of a heat sink panel, wherein a second side of the heat sink panel comprises a bottom-most surface of the main body;

at least one UVLE panel, operably connected to the heat sink, and operably connected to the at least one control board, wherein the at least one UVLE panel comprises at least one ultraviolet (UV) light-emitter (UVLE), wherein the bottom-most surface of the main body is located between the at least one UVLE panel and the heat sink such that the at least one UVLE is located below the at least one UVLE panel and below the main body, wherein the at least one UVLE is a solid-state light emitter;

a plurality of end plates removably attached to a first exterior side and a second exterior side of the main body;

a plurality of wheel assemblies connected to the main body; and at least one speed sensor operably connected to the at least one control board, wherein the at least one speed sensor is configured to detect data on the speed of the main body and transmit the data to the at least one control board.

2. The device of claim 1, further comprising at least one feedback system mounted to or within at least one of the handle or the main body.

3. The device of claim 2, wherein the at least one feedback system is a haptic feedback system.

4. The device of claim 2, wherein the at least one feedback system is an audio feedback system.

5. The device of claim 2, wherein the at least one feedback system is a visual feedback system.

6. The device of claim 1, wherein the at least one speed sensor is an accelerometer.

7. The device of claim 1, wherein the at least one speed sensor is a light sensor that detects motion of a wheel in one of the plurality of wheel assemblies via alternating colors on a surface of the wheel.

8. The device of claim 1, wherein the at least one speed sensor is a laser motion sensor that detects surface motion of a wheel in one of the plurality of wheel assemblies.

9. The device of claim 1, wherein the at least one speed sensor is a physical roller contact sensor that reads the rotations and speed of a wheel in one of the plurality of wheel assemblies or a roller in contact with the wheel.

10. The device of claim 1, wherein the at least one speed sensor is a reed switch with a rotation magnet on a wheel in one of the plurality of wheel assemblies.

11. The device of claim 1, wherein the at least one UVLE emits UV light in the UVC range.

12. The device of claim 1, wherein the at least one UVLE emits UV light with a 250 nm wavelength.

13. The device of claim 1, wherein the at least one control board is configured to adjust the power provided to the at least one UVLE based on speed data received from the at least one speed sensor.

14. The device of claim 1, wherein the speed sensor is located on at least one of the plurality of end plates or the at least one control board.

15. The device of claim 1, further comprising at least one orientation sensor.

16. The device of claim 15, wherein the at least one control board is configured to adjust the power provided to the at least one UVLE based on orientation data received from the at least one orientation sensor.

17. The device of claim 1, further comprising a plurality of vents in each of the plurality of end plates.

18. The device of claim 1, wherein the main body is manufactured from extruded metal.

19. The device of claim 1, further comprising at least one UVLE shield extending over the at least one UVLE panel.

* * * * *